(12) United States Patent
Nagano et al.

(10) Patent No.: US 8,309,319 B2
(45) Date of Patent: Nov. 13, 2012

(54) FLUORESCENT PROBE FOR MEASUREMENT OF UDP-GLUCURONOSYLTRANSFERASE

(75) Inventors: Tetsuo Nagano, Tokyo (JP); Yasuteru Urano, Kanagawa (JP); Rie Tomiyasu, Aichi (JP)

(73) Assignee: The University of Tokyo, Tokyo (JP)

( * ) Notice: Subject to any disclaimer, the term of this patent is extended or adjusted under 35 U.S.C. 154(b) by 289 days.

(21) Appl. No.: 12/527,793

(22) PCT Filed: Feb. 26, 2008

(86) PCT No.: PCT/JP2008/053218
§ 371 (c)(1),
(2), (4) Date: Aug. 3, 2010

(87) PCT Pub. No.: WO2008/105376
PCT Pub. Date: Sep. 4, 2008

(65) Prior Publication Data
US 2010/0297681 A1    Nov. 25, 2010

Related U.S. Application Data

(60) Provisional application No. 60/903,534, filed on Feb. 27, 2007.

(51) Int. Cl.
*C12Q 1/48* (2006.01)

(52) U.S. Cl. .......................... 435/15; 435/184; 549/385

(58) Field of Classification Search .................... 435/15; 549/385
See application file for complete search history.

(56) References Cited

U.S. PATENT DOCUMENTS

| | | | |
|---|---|---|---|
| 7,332,278 B2 | 2/2008 | Lowery et al. | |
| 7,355,010 B2 | 4/2008 | Lowery et al. | |
| 7,378,505 B2 | 5/2008 | Lowery et al. | |
| 2004/0219510 A1 | 11/2004 | Lowery et al. | |
| 2005/0239142 A1 | 10/2005 | Lowery et al. | |
| 2006/0172335 A1 | 8/2006 | Lowery et al. | |
| 2009/0258434 A1 | 10/2009 | Nagano et al. | |

FOREIGN PATENT DOCUMENTS

WO    2004/068115    8/2004

OTHER PUBLICATIONS

Japanese and English versions of the International Preliminary Report on Patentability of Chapter 1 (Written Opinion of the International Searching Authority), PCT/JP2008/053218 Sep. 1, 2009.
Y. Urano et al., "Evolution of Fluorescein as a Platform for Finely Tunable Fluorescence Probes", J. Am. Chem. Soc., vol. 127, No. 13, pp. 4888-4894, 2005.
T. Ueno et al., "Rational principles for Modulating Fluorescence Properties of Fluorescein", J. Am. Chem. Soc., vol. 126, No. 43, pp. 14079-14085, 2004.
K. Tanaka et al., "Rational design of Fluorescein-Based Fluorescence Probes. Mechanism-Based Design of a Maximum Fluorescence Probe for Singlet Oxygen", J. Am. Chem. Soc., vol. 123, No. 11, pp. 2530-2536, 2001.
U.S. Appl. No. 12/526,677, filed Aug. 11, 2009.
U.S. Appl. No. 12/447,723, filed Apr. 29, 2009.
U.S. Appl. No. 12/527,898, filed Aug. 20, 2009.
International Search Report for International Application No. PCT/JP2008/053218, May 27, 2008.

*Primary Examiner* — Bernard Dentz
(74) *Attorney, Agent, or Firm* — Greenblum & Bernstein, P.L.C.

(57) ABSTRACT

A fluorescent probe for measurement of UDP-glucuronosyltransferase, which comprises a fluorescein derivative, wherein in the fluorescein derivative, the 2-carboxy group on the benzene ring of fluorescein is replaced with another monovalent substituent, provided that said substituent is a substituent other than sulfo group, and the substituent does not have carboxy group or sulfo group, and wherein the fluorescein derivative may have an arbitrary substituent at a position on the benzene ring other than the 2-position, and the fluorescein derivative may have a substituent selected from the group consisting of an alkoxy group and a halogen atom at the 2-position and/or the 7-position of fluorescein.

8 Claims, 5 Drawing Sheets

FLUORESCENT PROBE FOR MEASUREMENT OF UDP-GLUCURONOSYLTRANSFERASE

TECHNICAL FIELD

The present invention relates to a fluorescent probe for measurement of UDP-glucuronosyltransferase.

BACKGROUND ART

Comprehensive measurements of reactivities and inhibitory activities of various medicaments for drug-metabolizing enzymes are very important for predicting onset of side effects, medicament interactions and the like induced by administration of the medicaments. For example, cytochrome P-450 is a typical drug-metabolizing enzyme, and since a medicament having an inhibitory action on cytochrome P-450 may produce side effects, high throughput screening (HTS) systems have been developed, which enable efficient measurement of inhibitory activities of various medicaments against cytochrome P-450. However, there are also medicaments which are detoxified by UDP-glucuronosyltransferase, which is a conjugation enzyme (henceforth also abbreviated as "UGT" in this specification), in the metabolic processes of the medicaments, and there are many cases where a drug-metabolizing enzyme other than cytochrome P-450 plays a more important role.

UGT is a kind of phase II conjugation reaction enzymes, and metabolizes endogenous substances such as bilirubin and steroid hormones and exogenous substances such as medicaments, carcinogens and environmental pollutants as substrates, and responsible for about 15% of the metabolism of major medicaments. And there have been made reports about a possibility that elimination kinetics of medicaments such as acetaminophen, lamotrigine and lorazepam are changed by variation of the metabolic activity of UTG based on genetic polymorphism of UGT isozymes. Among them, a research that most definitely demonstrates the influence of the UGT gene polymorphism includes the research on the gene polymorphism of UGT1A1, a kind of the UGT isozyme responsible for metabolism and detoxification of the active metabolite SN-38 of irinotecan hydrochloride (topoisomerase I inhibitor) which is used for the therapeutic treatment of solid tumors such as metastatic colon cancer (Isomura, M., et al., Gan To Kagaku Ryoho., 32, 1908, 2005).

Irinotecan hydrochloride, which is a prodrug, is converted into the active type, SN-38, by carboxy esterase, and then SN-38 undergoes glucuronidation by UGT1A1 and thereby detoxified into the inactive type in vivo. However, in patients with low UGT1A1 activity, the conversion from the active type into the inactive type is insufficient, thus SN-38 stays in the body for a long period of time, and therefore risk associated with onset of side effects increases. Where a medicament to be detoxified by UGT such as irinotecan hydrochloride is administered, this result also suggests a possibility that more critical side effects may be induced by UGT1A1 inhibition caused by the use of other combined medicaments. Therefore, in recent years, UGT has attracted much attention as a drug-metabolizing enzyme, and especially UGT1A1 isozymes has been focused.

From the viewpoint mentioned above, it is necessary, in the screening of candidates for drug development, to investigate UGT inhibitory action of the candidate compounds for predicting onset of side effects. However, the currently available test methods are quantitative analysis methods using purification apparatuses such as HPLC, and thus they have a problem in that they are inconvenient and time consuming. Therefore, it is desired to develop an HTS system which enables simple and short time measurement of UGT inhibitory activity of lots of test compounds. In particular, there is desired an HTS system which enables convenient and rapid measurement of UGT inhibitory activity by using a fluorescent probe with which the UGT activity can be highly sensitively measured.

Scopoletin having the coumarin structure was found in recent years as a probe for detecting the UGT activity by fluorescence (http://www.bdbiosciences.com/discovery_labware/gentest/products/pdf/). However, this probe is a short wavelength excitation type probe, which emits fluorescence with an excitation light of around 300 nm, and thereby because the probe is easily influenced by intracellular background fluorescence, the probe has a problem in that it is inapplicable to tests using cells or tissues. The probe also has a problem in that its sensitivity is low due to its low molar absorption coefficient.

DISCLOSURE OF THE INVENTION

Object to be Achieved by the Invention

An object of the present invention is to provide a means for measuring UDP-glucuronosyltransferase (UGT) activity by fluorescence. More specifically, the object of the present invention is to provide a fluorescent probe which enables highly sensitive measurement of the UGT activity.

Means for Achieving the Object

Fluorescein is a fluorescent compound which has superior fluorescence characteristics in water and has been used as a mother nucleus of many fluorescent probes. The inventors of the present invention conducted various researches under assumption that it might be possible to provide a fluorescent probe for measurement of UGT activity by utilizing the fluorescein structure instead of the coumarin structure as a mother nucleus of fluorescent probe for measurement of UGT activity. However, fluorescein itself lacked reactivity with UGT in vitro, and thus the inventors concluded that it was impossible to use fluorescein as a fluorescent probe for measurement of UGT activity. The inventors of the present invention further conducted researches, and surprisingly found that derivatives of fluorescein, in which the 2-carboxy group on the benzene ring was esterified, or replaced with amino group and then amidated, had improved reactivity to UGT. The inventors also found that other fluorescein derivatives in which the 2-carboxy group on the benzene ring was substituted by another group also had reactivity to UGT, and they concluded that reaction of fluorescein and UGT was inhibited by the 2-carboxy group on the benzene ring of fluorescein. The present invention was accomplished on the basis of the aforementioned findings.

The present invention thus provides a fluorescent probe for measurement of UDP-glucuronosyltransferase, which comprises a fluorescein derivative [in the fluorescein derivative, the 2-carboxy group on the benzene ring of fluorescein is replaced with another monovalent substituent (this substituent is a substituent other than sulfo group, and the substituent does not have carboxy group or sulfo group), the fluorescein derivative may have an arbitrary substituent at a position on the benzene ring other than the 2-position, and the fluorescein derivative may have a substituent selected from the group consisting of an alkoxy group and a halogen atom at the 2-position and/or the 7-position of fluorescein].

In the aforementioned invention, arbitrary isozymes of UDP-glucuronosyltransferase or arbitrary mixtures thereof may be used as the measurement object. UGT1A1 is preferred.

Further, the present invention also provides a method for measurement of UDP-glucuronosyltransferase activity, which comprises the step of reacting UDP-glucuronosyltransferase and the aforementioned fluorescein derivative, and detecting change of fluorescence before and after the reaction.

Furthermore, the present invention also provides a method for screening candidate compounds of medicament, which comprises the step of reacting UDP-glucuronosyltransferase and the aforementioned fluorescein derivative in the presence and absence of a test compound, and detecting changes of fluorescence before and after the reactions, and the step of, when difference is observed between the changes of fluorescence detected in the presence and absence of the test compound, determining that the test compound has an action on UDP-glucuronosyltransferase, and is unsuitable as a candidate compound of medicament.

BEST MODE FOR CARRYING OUT THE INVENTION

Figure 1:
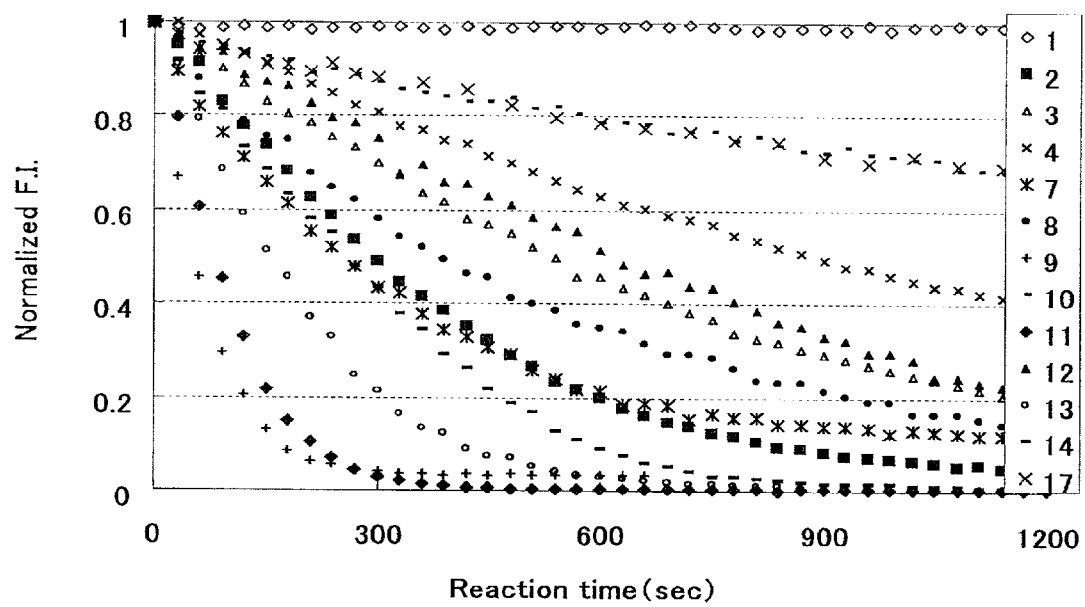
FIG. 1 shows results of measurement of reactivity of a fluorescein derivative in which the 2-carboxy group on the benzene ring of fluorescein is replaced with another substituent with UGT1A1 according to the fluorescence method.

The monovalent substituent which replaces the carboxy group of the 2-position on the benzene ring of fluorescein is a substituent other than sulfo group, and this substituent does not have carboxy group or sulfo group. Examples of the monovalent substituent include, for example, hydrogen atom, an alkyl group, an alkenyl group, an alkynyl group, an alkoxy group, nitro group, amino group, cyano group, an alkoxycarbonyl group, an alkanoylamino group, an aryl group, a heteroaryl group, an aroylamino group, a heteroaroylamino group and the like, but it is not limited to these examples.

As the alkyl group, for example, linear, branched or cyclic $C_1$-$C_6$ alkyl groups, a $C_1$-$C_6$ alkyl group consisting of a combination thereof and the like can be used. Examples include, methyl group, ethyl group, n-propyl group, isopropyl group, cyclopropyl group, n-butyl group, isobutyl group, sec-butyl group, tert-butyl group, cyclopropylmethyl group, and the like. The above explanation is similarly applied to an alkyl moiety of other substituents having the alkyl moiety (an alkoxy group, an alkoxycarbonyl group, an alkanoyl group and the like).

The alkenyl group may be a linear, branched or cyclic alkenyl group, or an alkenyl group consisting of a combination of such alkyl groups, and may contain one or two double bonds. Examples include, for example, a $C_2$-$C_6$ alkenyl group, and the like, and specific examples include vinyl group, 1-propenyl group, allyl group, isopropenyl group, 1-butenyl group, and the like.

The alkynyl group may be a linear or branched alkynyl group, and may contain one or two triple bonds, or one triple bond and one double bond. Examples of the alkynyl group include, ethynyl group, 1-propynyl group, 2-propynyl group, 1-butynyl group, and the like.

As the aryl group, a monocyclic or condensed polycyclic aromatic hydrocarbon group can be used, and examples include, phenyl group, naphthyl group, and the like. As the heteroaryl group, a monocyclic or condensed polycyclic aromatic group containing one or more heteroatoms as ring-constituting atoms can be used. Examples of the heteroatom include, nitrogen atom, oxygen atom, sulfur atom, and the like, and when two or more heteroatoms are contained, they may be the same or different. More specifically, examples include furyl group, thienyl group, pyrrolyl group, pyridyl group, imidazolyl group, pyrimidyl group, and the like. The aryl group or the heteroaryl group may be partially saturated, or completely saturated. The above explanation is similarly applied to an aryl moiety or heteroaryl moiety of a group having the aryl moiety or heteroaryl moiety (an aroyl group, a heteroaroyl group, and the like).

The aforementioned fluorescein derivative may have an arbitrary substituent at a position other than the 2-position of the benzene ring. Two or more of such substituents may exist, and when two or more substituents exist, they may be the same or different. Adjacent substituents may bind together to form a ring structure.

Examples of the substituent which can exist at a position other than the 2-position of the benzene ring include, for example, an alkyl group, an alkenyl group, an alkynyl group, an alkoxy group, an alkoxycarbonyl group, hydroxy group, amino group, carboxyl group, a halogen atom (examples of the halogen atom include fluorine atom, chlorine atom, bromine atom, iodine atom and the like), and the like, but not limited to these examples.

The aforementioned fluorescein derivative may have a substituent selected from the group consisting of an alkoxy group and a halogen atom at the 2-position and/or the 7-position. As the alkoxy group, methoxy group is preferred. As the halogen atom, fluorine atom or chlorine atom is preferred, and chlorine atom is particularly preferred.

As the aforementioned fluorescein derivative, a fluorescein derivative, wherein the 2-carboxy group on the benzene ring of fluorescein is replaced with an alkyl group, preferably methyl group; a fluorescein derivative, wherein the 2-carboxy group on the benzene ring of fluorescein is replaced with an alkyl group, preferably methyl group, and an alkoxy group, preferably methoxy group, is introduced at the 4-position of the benzene ring; and such fluorescein derivatives as mentioned above, wherein an alkoxy group, preferably methoxy group, is introduced at the 2-position and/or the 7-position, preferably at the 2-position and the 7-position, are preferred. Further, a fluorescein derivative, wherein the 2-carboxy group on the benzene ring of fluorescein is replaced with 2-naphthoylamino group is also preferred. Furthermore, a fluorescein derivative, wherein the 2-carboxy group on the benzene ring of fluorescein is replaced with nitro group, and methyl group is introduced at the 4-position of the benzene ring is also preferred. However, the fluorescein derivative is not limited to these examples.

The aforementioned fluorescein derivative may form a salt depending on type of substituent. Type of the salt is not particularly limited, and it may be an acid addition salt, or a base addition salt. As a salt of the aforementioned fluorescein derivative, a physiologically acceptable salt is preferred. Specific examples of the salt include, acid addition salts including mineral acid salts such as hydrochlorides, sulfates and nitrates, and organic acid salts such as tartrates, p-toluenesulfonates, malates, oxalates and acetates, metal salts such as sodium salts, potassium salts, magnesium salts and calcium salts, ammonium salts, organic amine salts such as monomethylamine salts and triethylamine salts, and the like. Moreover, the aforementioned fluorescein derivative or a salt thereof may form a hydrate or a solvate, and these arbitrary hydrates and solvates are fall within the scope of the present invention.

Some of the aforementioned fluorescein derivatives are known compounds, and methods for preparing various fluorescein derivatives are known. Accordingly, those skilled in the art can easily prepare the aforementioned fluorescein derivatives (J. Am. Chem. Soc., 127, pp. 4888-4894, 2005; J. Am. Chem. Soc., 126, pp. 14079-14085, 2004; J. Am. Chem. Soc., 123, pp. 2530-2536, 2001).

The probe for measurement of UDP-glucuronosyltransferase of the present invention is characterized in that the probe contains the aforementioned fluorescein derivative, and when the aforementioned fluorescein derivative reacts with UDP-glucuronosyltransferase to form an O-glycoside compound, the probe shows a change in the fluorescent characteristics or absorbance before and after the reaction. Typically, when the aforementioned fluorescein derivative originally emits fluorescence, fluorescence thereof is substantially quenched after the reaction with UDP-glucuronosyltransferase, or when the derivative is a fluorescein derivative of which fluorescence is appropriately decreased according to the PeT theory described later, the derivative becomes to substantially emit fluorescence after the reaction. By detecting change of the fluorescence characteristics of the aforementioned fluorescein derivative before and after the reaction, presence of UDP-glucuronosyltransferase and the like can be measured. Whether the aforementioned fluorescein derivative originally emits fluorescence or whether the derivative originally is substantially non-fluorescent can be easily predicted according to the PeT theory already proposed by the inventors of the present invention (J. Am. Chem. Soc., 126, pp. 14079-14085, 2004; J. Am. Chem. Soc., 125, pp. 8666r8671, 2003), and those skilled in the art can appropriately design and prepare a desired fluorescein derivative according to an object of the measurement, and can use the derivative as the probe of the present invention for measurement of UDP-glucuronosyltransferase. The term "measurement" used herein should be construed in its broadest sense, including quantitative and qualitative measurements. Further, the probe for measurement of UDP-glucuronosyltransferase of the present invention may be herein generally called "fluorescent probe", or the probe for fluorescence measurement and the probe for absorbance measurement may be representatively called "fluorescent probe".

The method for using the fluorescent probe of the present invention is not particularly limited, and the probe can be used in the same manner as conventionally known fluorescent probes. In general, the aforementioned fluorescein derivative may be dissolved in an aqueous medium such as physiological saline or a buffered solution, or in a mixture of an aqueous medium and a water-miscible organic solvent such as ethanol, acetone, ethylene glycol, dimethyl sulfoxide, and dimethylformamide, and reacted with UDP-glucuronosyltransferase. By adding the resultant solution to a suitable buffered solution containing cells or tissues, and measuring fluorescence spectrum, the UDP-glucuronosyltransferase activity in the cells or tissues can also be measured. The fluorescent probe of the present invention may be combined with an appropriate additive and used in the form of a composition. For example, it may optionally be combined with additives such as buffers, dissolving aids, and pH modifiers.

The fluorescent probe of the present invention comprises a fluorescein derivative having the absorption maximum wavelength around 480 to 510 nm, which is less influenced by background fluorescence of cells or biological tissues, and a large molar absorption coefficient at a wavelength around 480 to 510 nm, and thus achieves highly sensitive measurement of UDP-glucuronosyltransferase activity. Therefore, the probe can be used for a method of screening candidate compounds of medicament.

Test compounds having a certain action on UDP-glucuronosyltransferase such as inhibitory action and activation action are generally unsuitable as candidate compounds of medicament. By using the fluorescent probe of the present invention, a large number of test compounds can be screened to detect test compounds having an action on UDP-glucuronosyltransferase, and it can be determined that such detected test compounds are unsuitable as candidate compounds of medicament. More specifically, UDP-glucuronosyltransferase and the aforementioned fluorescein derivative can be reacted in the presence and absence of a test compound using human UGT-expressing microsomes (baculovirus type), control microsomes, and the like, changes of fluorescence before and after the reactions can be measured, and when difference is observed between the changes of fluorescence detected in the presence and absence of the test compound, it can be determined that the test compound has an action on UDP-glucuronosyltransferase, and is unsuitable as a candidate compound of medicament.

EXAMPLES

The present invention will be more specifically explained with reference to examples. However, the scope of the present invention is not limited to the following examples.

Example 1

According to the following protocols, fluorescein (Compound 1), fluorescein derivatives in which the 2-carboxy group on the benzene ring of fluorescein was replaced with another substituent (Derivatives 2 to 16), and a conventional compound having the coumarin structure, scopoletin (Compound 17) were examined for reactivity with UGT1A1.

A solution of the following composition was prepared in a 3000 μL cuvette (total volume: 3000 μL)
Probe: fluorescein derivative (1 μM or 10 μM)
$MgCl_2$ (8 mM)
Alamethicin (0.025 mg/mL)
UDP-glucuronic acid (2 mM)
Adjusted to a total volume of 2940 μL with 0.1 M Tris-HCl buffer (pH 7.5)
↓
Addition of 60 μL of UGT1A1 microsome solution (5.0 mg/mL, final concentration: 0.1 mg/mL)
↓
Fluorescence or absorbance measurement with stirring or pipetting (37° C.)

In this example, when a fluorescent compound was used as a substrate, 1 μM solution of a fluorescein derivative was used, and fluorescence measurement was performed by irradiating an excitation light of 480 to 510 nm while the solution in a cuvett is stirred with stir bar; when scopoletin was used, 1 μM solution of scopoletin was used, and fluorescence measurement was performed by irradiating an excitation light of around 300 nm while the solution in a cuvett is stirred with stir bar; and then the decrease in the fluorescence intensity was observed as an index indicating advance of the reaction. Further, when a weakly fluorescent compound such as a compound having nitro group was used as a substrate, 10 μM solution of a fluorescein derivative was used, absorbance measurement was performed at 480 to 510 nm with pipetting a solution in a cuvette, and decrease of absorbance was observed as an index indicating advance of the reaction.

The following fluorescein derivatives were used as the substrate (in the following formulas, Me represents methyl group).

[Formula 1]

(1)
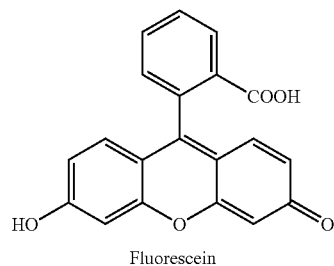
Fluorescein (2)
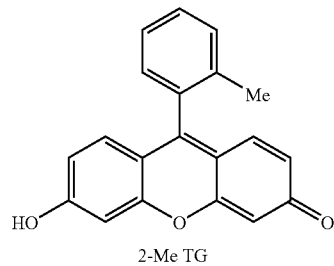
2-Me TG (3)
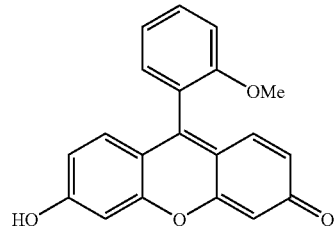

(4)
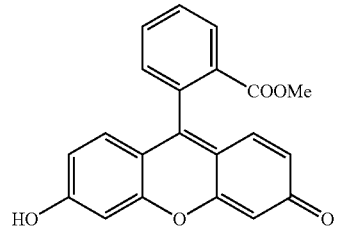

(5)
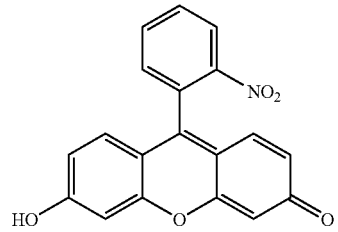

(6)
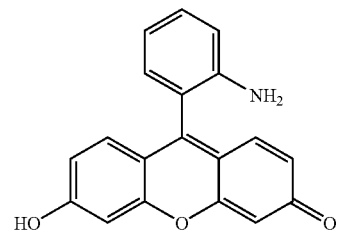

(7)
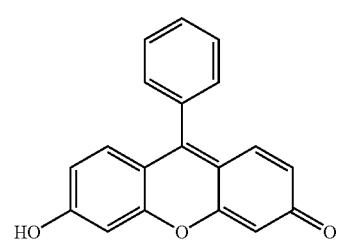

(8)
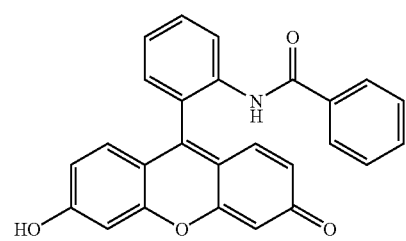

(9)
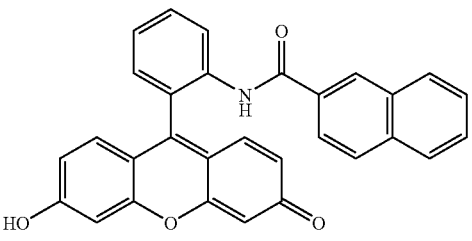

(10)
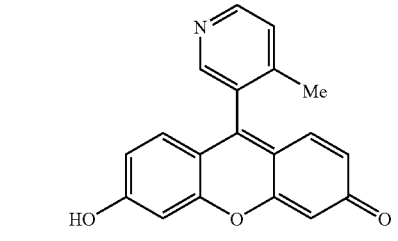

(11)
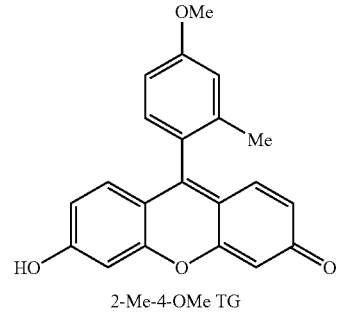
2-Me-4-OMe TG

-continued

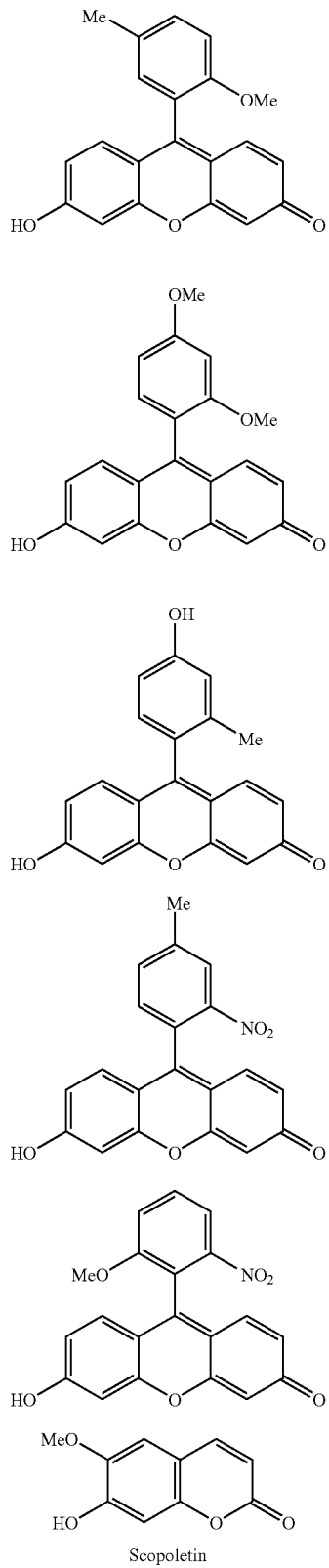

(12)
(13)
(14)
(15)
(16)
(17) Scopoletin

Figure 2:
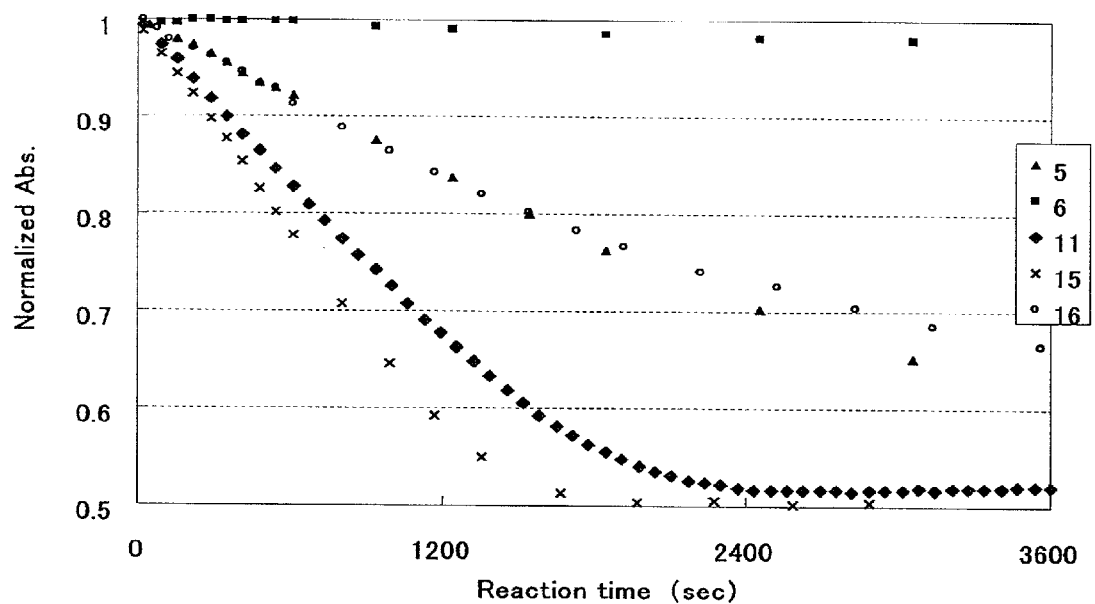
FIG. 2 shows results of measurement of reactivity of a fluorescein derivative in which the 2-carboxy group on the benzene ring of fluorescein is replaced with another substituent with UGT1A1 according to the absorbance method.

The results are shown in FIGS. 1 and 2. As clearly shown by these results, it was recognized that fluorescein (Compound 1) itself was completely unreactive with UGT1A1. On the other hand, it was confirmed that the fluorescein derivatives (Derivatives 2 to 16) in which the 2-carboxy group on the benzene ring of fluorescein was replaced with another substituent (hydrogen atom, an alkyl group, methoxy group, methoxycarbonyl group, nitro group, amino group, and the like) were reacted with UGT1A1, and they showed a change in the fluorescence characteristics or absorbance as the reaction advanced. In particular, the fluorescein derivative in which the 2-carboxy group on the benzene ring of fluorescein was replaced with methyl group, and methoxy group was introduced at the 4-position of the benzene ring (Derivative 11, henceforth referred to as "2-Me-4-OMe-TG") had a superior property suitable for use in measurement of the UGT activity, i.e., high decrease rate of fluorescence, and decrease of fluorescence intensity to 0.1% or less. Further, the fluorescein derivative in which the 2-carboxy group on the benzene ring of fluorescein was replaced with 2-naphthoylamino group (Derivative 9) also had a property similar to that of "2-Me-4-OMe-TG". Furthermore, the fluorescein derivative in which the 2-carboxy group on the benzene ring of fluorescein was replaced with nitro group, and methyl group was introduced at the 4-position of the benzene ring (Derivative 15) showed higher decrease rate of absorbance compared with that of "2-Me-4-OMe-TG". The fluorescein derivative in which the 2-carboxy group on the benzene ring of fluorescein was replaced with amino group (Derivative 6) also showed the reactivity, although it was weak.

Example 2

Figure 3A:
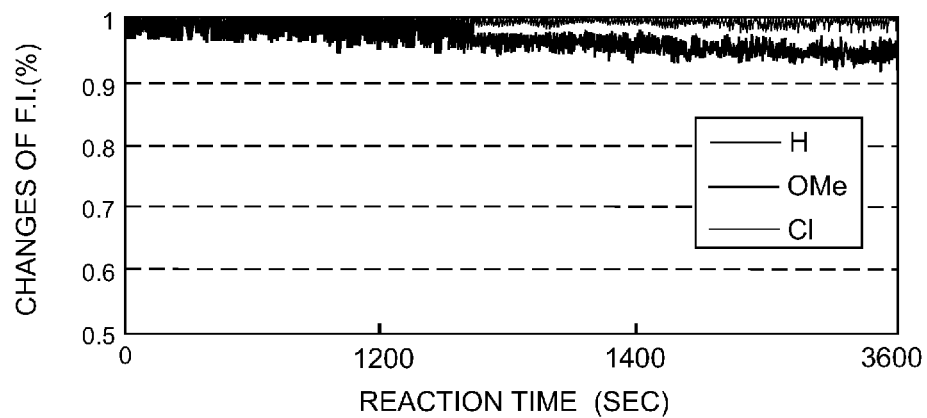
FIG. 3(A) shows no decrease in fluorescence from any of the three compounds, indicating a lack of reactivity.
Figure 3B:
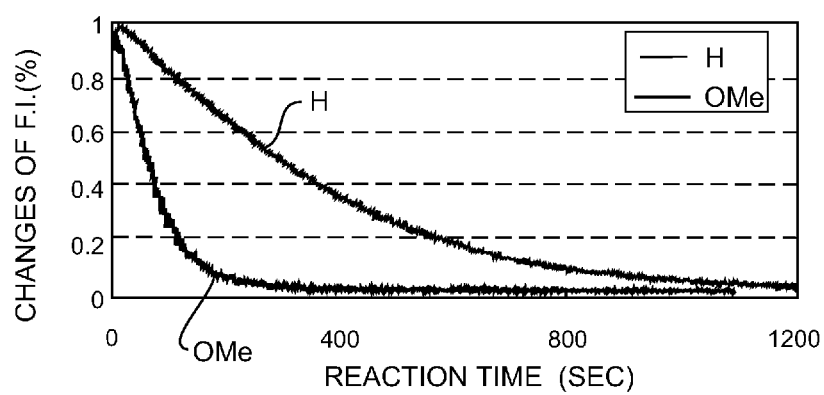
FIG. 3 shows results of measurement of reactivity of fluorescein derivatives in which methoxy group or chlorine atom is introduced at the 2-position and/or the 7-position of fluorescein with UGT1A1. (A), (B), and (C) show the results for the compounds mentioned in Example 2, respectively.
Figure 3C:
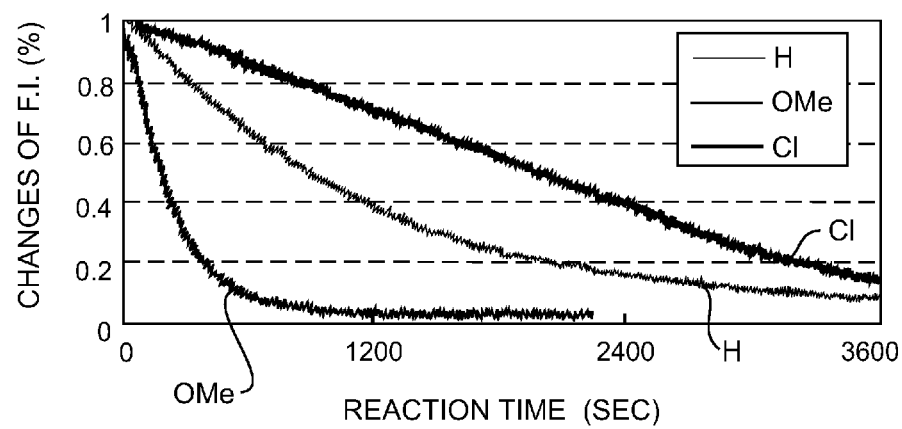

According to the following protocols, fluorescein derivatives in which methoxy group or chlorine atom was introduced at the 2-position and/or the 7-position of fluorescein (the compounds described in (A), (B), and (C) mentioned below) were examined for reactivity with UGT1A1. The results are shown in FIG. 3. As seen in FIG. 3, (C), a tendency was observed that a decrease rate of fluorescence of fluorescein methyl ester (Derivative 4) was reduced by the introduction of chlorine atom, whilst it was confirmed that a decrease rate of fluorescence was increased by the introduction of methoxy group. The same results were also obtained when methoxy group was introduced into 2-MeTG (Derivative 2) as seen in FIG. 3, (B). FIG. 3(A) shows no decrease in fluorescence from any of the three compounds, indicating a lack of reactivity.

A solution of the following composition was prepared in a 3000 μL cuvette (total volume: 3000 μL)

Probe: the compound described in (A), (B), or (C) mentioned below (1 μM)

MgCl$_2$ (8 mM)

Alamethicin (0.025 mg/mL)

UDP-glucuronic acid (2 mM)

Adjusted to a total volume of 2940 μL with 0.1 M Tris-HCl buffer (pH 7.5)

↓

Addition of 60 μL of UGT1A1 microsome solution (5.0 mg/mL, final concentration: 0.1 mg/mL)

↓

Fluorescence measurement with stirring (37° C.)

[Formula 2]

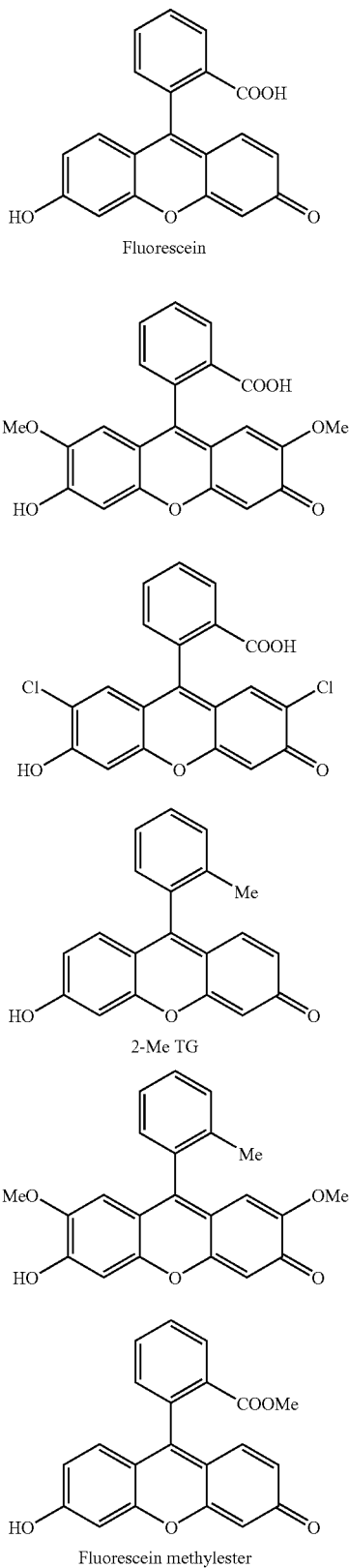

(A) Fluorescein (B) 2-Me TG (C) Fluorescein methylester

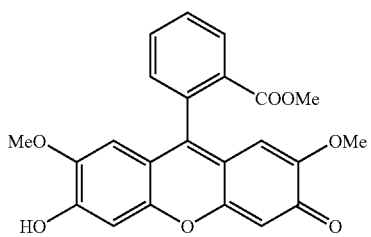

Example 3

Figure 4:
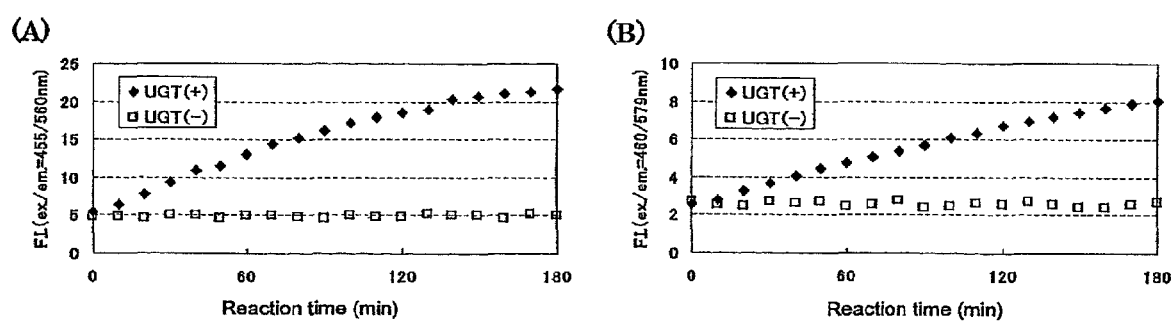
FIG. 4 shows results of measurement of reactivity of fluorescence increasing type probes with UGT1A1. (A) shows the results for 6-carboxyfluorescein dimethyl ester, and (B) shows the results for 5,6-dicarboxyfluorescein trimethyl ester.

The fluorescein derivatives of fluorescence decreasing type, of which fluorescence is decreased by a reaction with UGT, were obtained in Examples 1 and 2. Further researches were conducted in order to provide fluorescein derivatives of fluorescence increasing type of which fluorescence is increased by a reaction with UGT. Functionally, the structure of fluorescein can be recognized as two parts having different functions, i.e. the benzene ring moiety and the xanthene ring moiety. By appropriately choosing substituents on the benzene ring moiety among them, fluorescence thereof can be controlled by using PeT (J. Am. Chem. Soc., 123, pp. 2530-2536, 2001). On the other hand, it is known that the electron donating ability of the xanthene ring moiety is decreased by conversion of the phenolic hydroxy group of the moiety from phenolate type to O-glycoside type (J. Am. Chem. Soc., 127, pp. 4888-4894, 2005). Therefore, it is considered that there can be developed a fluorescence increasing type fluorescein derivative of which fluorescence is quenched by PeT before the reaction with UGT when the fluorescein derivative is a phenolate type, and fluorescence is emitted after the reaction with UGT when the fluorescein derivative is an O-glycoside type, by appropriately choosing the substituents on the benzene ring moiety (J. Am. Chem. Soc., 126, pp. 14079-14085, 2004). From such a point of view, 6-carboxyfluorescein dimethyl ester and 5,6-dicarboxyfluorescein trimethyl ester were designed as fluorescence increasing (d-PeT) type fluorescein derivatives, and reactivity thereof with UGT1A1 was confirmed. The results are shown in FIG. 4. As seen in FIG. 4 (A) for 6-carboxyfluorescein dimethyl ester and FIG. 4 (B) for 5,6-dicarboxyfluorescein trimethyl ester, increase of fluorescence intensity was observed with passage of the reaction time, and thus it was demonstrated that they functioned as fluorescence increasing (d-PeT) type fluorescent probes, which enable detection of progress of a UGT reaction by the increase of fluorescence.

[Formula 3]

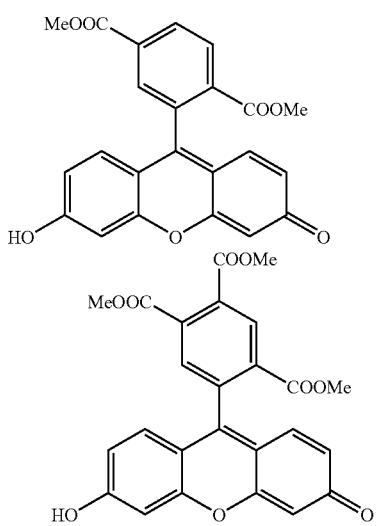

Example 4

According to the following protocols, it was verified whether inhibitory activity of a UGT inhibitor could be detected by fluorescence in a 96-well microplate by using the fluorescein derivative of the present invention. As the fluorescein derivative, 2-Me-4-OMe-TG was used, and as the UGT inhibitor, β-estradiol and chrysin were used.

[Formula 4]

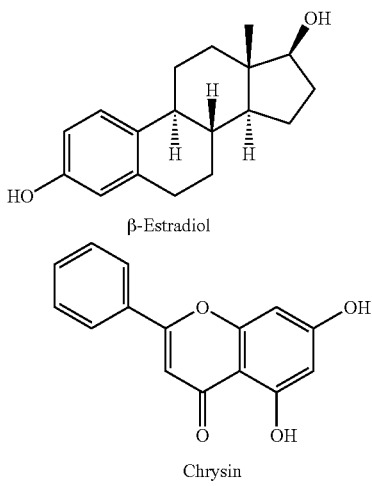

A solution of the following composition was prepared in wells of a 96-well plate (total volume: 160 μL)

Probe: 2-Me-4-OMe-TG (0.2 μM)
UGT inhibitor (0, 1, 5, 10, 50, 100 μM)
$MgCl_2$ (8 mM)
Alamethicin (0.025 mg/mL)
UDP-glucuronic acid (2 mM)
Adjusted to a total volume of 160 μL with 0.1 M Tris-HCl buffer (pH 7.5)
↓
Addition of 40 μL of UGT1A1 or control microsome solution (5.0 mg/mL, final concentration: 0.1 mg/mL).

Figure 5:
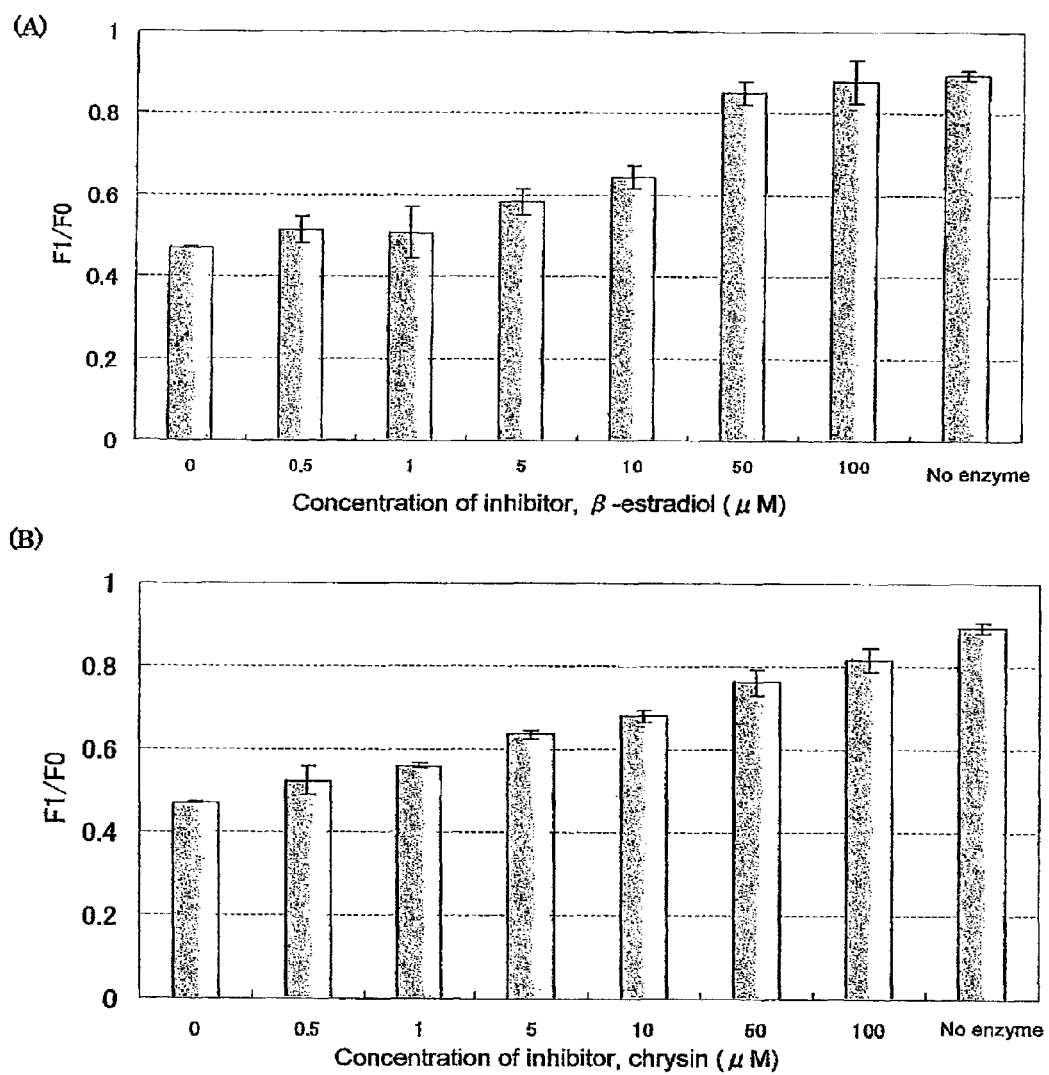
FIG. 5 shows results of measurement of inhibitory effect of UGT activity by UGT1A1 inhibitors, β-estradiol and chrysin, using the fluorescent probe of the present invention. (A) shows the results for β-estradiol, and (B) shows the results for chrysin.

As the control microsome solution, a microsome solution in which UGT1A1 was not expressed was used at a UGT inhibitor concentration of 0 μM
↓
Shaking of the mixture was carried out for 180 seconds, and fluorescence measurement (room temperature) performed after 230 seconds from the start of the reaction The results are shown in FIG. 5. A tendency was observed that change of fluorescence intensity decreased, i.e., progress of the reaction is inhibited, as the UGT inhibitor increased. These results demonstrated that an HTS system using a 96-well microplate or the like could be constructed by using 2-Me-4-OMe-TG.

Example 5

Synthesis of Compounds 2,7-Dimethoxyfluorescein, methyl ester thereof, and 2,7-dimethoxyfluorescein derivative were synthesized by a condensation reaction under an acidic condition according to the conventional methods (J. Am. Chem. Soc., 126, pp. 14079-14085, 2004; J. Am. Chem. Soc., 123, pp. 2530-2536, 2001). The 2,7-dimethoxyfluorescein derivative was obtained by methylating a 2,7-dihydroxyfluorescein derivative with methyl iodide (in the following scheme, Me represents methyl group).

[Formula 5]

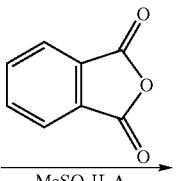
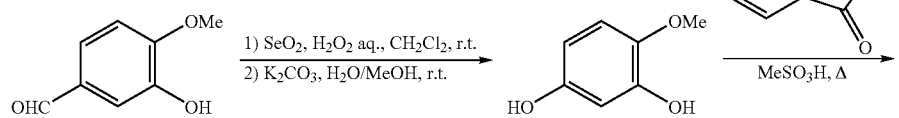

-continued

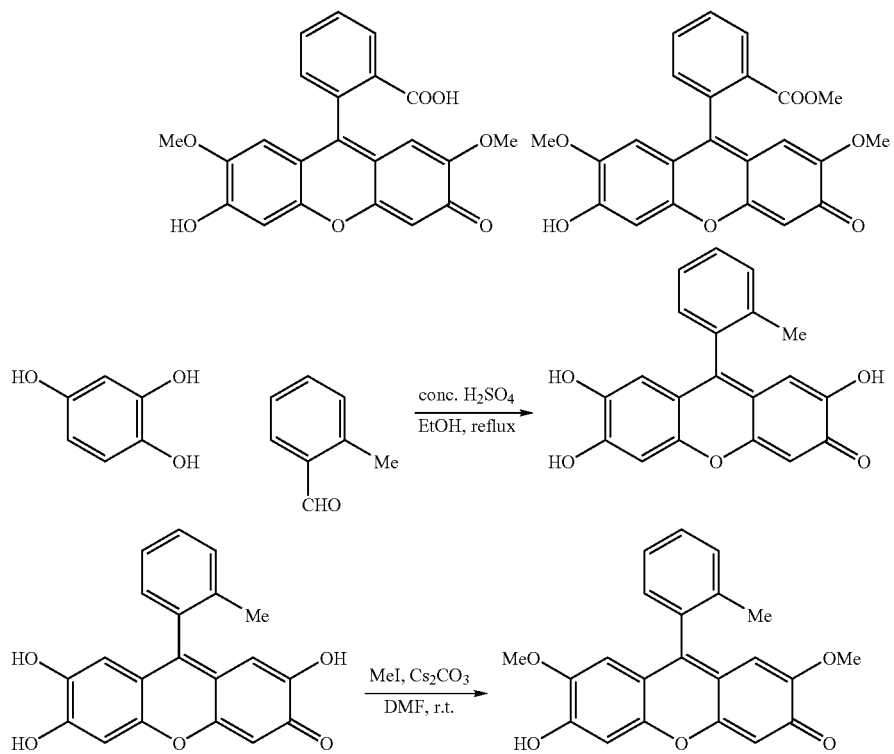

TABLE 1

| | |
|---|---|
| ![structure] | $^1$H-NMR (CD$_3$OD, 300 MHz) δ: 1.98 (s, 3H), 3.56 (s, 6H), 6.30 (s, 2H), 6.39 (s, 2H), 7.20 (d, 1H, J = 7.3 Hz), 7.36-7.49 (m, 3H). HRMS (ESI$^-$) Calcd for M − H; 361.10760 found; 361.10495 (−2.65 mmu). |
| ![structure] | $^1$H-NMR (CD$_3$OD, 300 MHz) δ: 3.55 (s, 3H), 3.59 (s, 6H), 6.27 (s, 2H), 6.78 (s, 2H), 7.48 (dd, 1H, J = 7.5 Hz, 1.1 Hz), 7.77 (td, 1H, J = 7.6 Hz, 1.3 Hz), 7.86 (td, 1H, J = 7.5 Hz, 1.3 Hz), 8.25 (dd, 1H, J = 7.8 Hz, 1.2 Hz). $^{13}$C-NMR (CD$_3$OD, 75 MHz) δ 52.9, 56.2, 104.2, 105.5, 116.4, 131.2, 131.8, 132.0, 132.1, 134.1, 135.8, 151.6, 151.9, 155.0, 167.5, 179.1. HRMS (ESI$^+$) Calcd for M + H; 407.11308 found; 407.11030 (−2.78 mmu). |
| ![structure] | $^1$H-NMR (CD$_3$OD, 300 MHz) δ: 3.50 (s, 6H), 6.17 (s, 2H), 6.67 (s, 2H), 7.29 (d, 1H, J = 7.5 Hz), 7.64 (t, 1H, J = 7.2 Hz), 7.72 (t, 1H, J = 7.2 Hz), 8.13 (d, 1H, J = 7.5 Hz). $^{13}$C-NMR (CD$_3$OD, 75 MHz) δ: 56.3, 104.1, 106.6, 115.1, 130.4, 131.0, 131.1, 132.0, 134.4, 139.6, 150.4, 153.7, 163.7, 169.3. HRMS (ESI$^+$) Calcd for M + H; 393.09743 found; 393.09666 (−0.77 mmu). |

INDUSTRIAL APPLICABILITY

The fluorescent probe provided by the present invention is useful as a means for highly sensitively measuring UDP-glucuronosyltransferase activity on the basis of fluorescence.

What is claimed is:

1. A probe for measurement of UDP-glucuronosyltransferase which comprises a fluorescein derivative, wherein, in the fluorescein derivative, the 2-carboxy group on the benzene ring of fluorescein is replaced with another monovalent substituent, provided that said substituent is a substituent other than sulfo group, and the substituent does not have carboxy group or sulfo group, and wherein the fluorescein derivative may have an arbitrary substituent at a position on the benzene ring other than the 2-position, and the fluorescein derivative may have a substituent selected from the group consisting of an alkoxy group and a halogen atom at the 2-position and/or the 7-position of fluorescein.

2. The probe according to claim 1, which is for fluorescence or absorbance measurement.

3. The probe according to claim 1, wherein the fluorescein derivative is a fluorescein derivative in which the 2-carboxy group on the benzene ring of fluorescein is replaced with an alkyl group; a fluorescein derivative in which the 2-carboxy group on the benzene ring of fluorescein is replaced with an alkyl group, and an alkoxy group is introduced at the 4-position of the benzene ring; or such a fluorescein derivative as mentioned above in which an alkoxy group is introduced at the 2-position and/or the 7-position.

4. The probe according to claim 1, wherein the fluorescein derivative is a fluorescein derivative in which the 2-carboxy group on the benzene ring of fluorescein is replaced with 2-naphthoylamino group.

5. The probe according to claim 1, wherein the fluorescein derivative is a fluorescein derivative in which the 2-carboxy group on the benzene ring of fluorescein is replaced with nitro group, and methyl group is introduced at the 4-position of the benzene ring.

6. The probe according to claim 1, wherein UDP-glucuronosyltransferase is UGT1A1.

7. A method for measurement of UDP-glucuronosyltransferase activity, which comprises the step of reacting UDP-glucuronosyltransferase and the fluorescein derivative according to claim 1, and detecting change of fluorescence or absorbance before and after the reaction.

8. A method for screening candidate compounds of medicament, which comprises the step of reacting UDP-glucuronosyltransferase and the fluorescein derivative according to claim 1 in the presence and absence of a test compound, and detecting changes of fluorescence or absorbance before and after the reactions, and the step of, when difference is observed between the changes of fluorescence or absorbance detected in the presence and absence of the test compound, determining that the test compound has an action on UDP-glucuronosyltransferase, and is unsuitable as a candidate compound of medicament.

* * * * *